United States Patent [19]

Salomon

[11] Patent Number: 5,157,118
[45] Date of Patent: Oct. 20, 1992

[54] N-SUBSTITUTED THIO ALKYL PHENOTHIAZINES

[75] Inventor: Mary F. Salomon, Cleveland Heights, Ohio

[73] Assignee: The Lubrizol Corporation, Wickliffe, Ohio

[21] Appl. No.: 610,595

[22] Filed: Nov. 8, 1990

Related U.S. Application Data

[63] Continuation of Ser. No. 568,105, Aug. 16, 1990, Pat. No. 5,034,019, which is a continuation of Ser. No. 210,609, Jun. 28, 1988, abandoned, which is a continuation of Ser. No. 908,077, Sep. 16, 1986, Pat. No. 4,785,095.

[51] Int. Cl.$^5$ .................. C07D 279/22; C10M 135/36
[52] U.S. Cl. .......................... 544/38; 544/35; 252/47.0; 252/47.5; 44/334
[58] Field of Search .................. 544/35, 38, 39

[56] References Cited

U.S. PATENT DOCUMENTS

| | | | |
|---|---|---|---|
| 2,738,349 | 3/1956 | Gaillot et al. | 544/38 |
| 2,781,318 | 2/1957 | Cyphers | 252/47 |
| 2,837,518 | 6/1958 | Jacob et al. | 544/38 |
| 2,914,527 | 11/1959 | Winthrop et al. | 260/243 |
| 3,218,256 | 11/1965 | Edwards et al. | 252/47.5 |
| 3,344,068 | 9/1967 | Waight et al. | 252/47.5 |
| 3,376,224 | 4/1968 | Elliot et al. | 252/47.5 |
| 3,389,124 | 6/1968 | Sparks | 44/334 |
| 3,468,798 | 9/1969 | Panzer | 44/334 |
| 3,523,910 | 8/1970 | Randell | 252/402 |
| 3,536,706 | 10/1970 | Randell | 260/243 |
| 3,539,515 | 11/1970 | McCabe | 252/47.5 |
| 3,560,531 | 2/1971 | Normant | 260/389 |
| 3,689,484 | 9/1972 | Spilners | 260/243 A |
| 3,709,879 | 1/1973 | Amin et al. | 260/243 A |
| 3,803,140 | 4/1974 | Cook et al. | 260/243 A |
| 3,956,289 | 5/1976 | McGuigan et al. | 544/38 |
| 4,031,023 | 6/1977 | Musser et al. | 252/48.2 |
| 4,249,002 | 2/1981 | Eriksoo | 544/38 |
| 4,249,003 | 2/1981 | Eriksoo | 544/38 |
| 4,785,095 | 11/1988 | Salomon | 544/38 |
| 4,798,684 | 1/1989 | Salomon | 252/47.5 |
| 4,915,858 | 4/1990 | Salomon | 252/47.5 |
| 5,035,817 | 7/1991 | Salomon | 252/47.5 |

FOREIGN PATENT DOCUMENTS

| | | | |
|---|---|---|---|
| 538505 | 3/1957 | Canada | 544/38 |
| 1296477 | 5/1967 | France . | |
| 0933505 | 8/1963 | United Kingdom . | |
| 1140089 | 1/1969 | United Kingdom . | |
| 1347141 | 7/1974 | United Kingdom . | |
| 1438482 | 6/1976 | United Kingdom . | |

OTHER PUBLICATIONS

Schmitt et al, Soc. Chem.—France—(1959) pp. 1816-1818.

*Primary Examiner*—Ellen McAvoy
*Attorney, Agent, or Firm*—Forrest L. Collins; Frederick D. Hunter; David M. Shold

[57] ABSTRACT

This invention describes phenothiazine derivatives which are N-substituted and which contain an additional sulfur molecule in the N substituent.

1 Claim, No Drawings

N-SUBSTITUTED THIO ALKYL PHENOTHIAZINES

This is a continuation of copending application Ser. No. 568,105 filed on Aug. 16, 1990 now U.S. Pat. No. 5,034,019; which is a continuation of Ser. No. 07/210,609 filed Jun. 23, 1988 now abandoned which is a continuation of Ser. No. 06/908,077 filed Sep. 16, 1986, now U.S. Pat. No. 4,785,095.

BACKGROUND OF THE INVENTION

1. Field of the Invention

The compositions of the present invention are useful as oxidation inhibitors acting as oxygen-acceptors, peroxide decomposers and electron transfer agents in antioxidant processes.

2. Description of the Art

Phenothiazine compounds are known in lubricant products from the U.S. Pat. No. 2,781,318 issued Feb. 12, 1957 to Cyphers. The alkyl phenothiazines of Cyphers are alkylated on the phenylene rings of the phenothiazine structure. Cyphers does not show or suggest the alkylation of the amine nitrogen in phenothiazine. The Cyphers patent is directed to the utility of phenothiazine as an antioxidant and corrosion inhibiting additive for ester, polyester, polyether and other synthetic lubricants.

U.S. Pat. No. 3,536,706 issued Oct. 27, 1970 to Randell suggests that phenothiazines may be used as additives for synthetic lubricants. The phenothiazines particularly described by Randell are those containing tertiary alkyl substituents having from 4 to 12 carbon atoms on the aryl groups which make up the phenothiazine structure. Randell also discloses fused rings on the two phenylene groups which make up the phenothiazine structure. Stated otherwise, Randell allows the utilization of naphthalene for at least one of the two aryl groups in the phenothiazine structure.

U.S. Pat. No. 3,803,140 issued to Cook et al on Apr. 9, 1974 describes various tertiary alkyl derivatives of phenothiazine. N-alkyl substitution or N-alkenyl substitution is described on the phenothiazine structure. Ring alkylation when the phenothiazine is in the free nitrogen form is also shown. Cook et al express a preference for non-N substituted phenothiazine derivatives.

Cook et al also suggest that organic materials which are susceptible to oxidative degradation may benefit through the use of the compounds of their invention. Such uses include antioxidants for aliphatic hydrocarbons such as gasoline, lubricating oils, lubricating greases, mineral oils, waxes, natural and synthetic polymers such as rubber, vinyl, vinylidene, ethers, esters, amides and urethanes. The compounds of Cook et al are also suggested for stabilizing aldehydes, and unsaturated fatty acids or esters thereof. Still further utilities suggested by Cook et al include the stabilization of organo-metalloid substances such as silicone polymers. Another class of uses of the compounds of Cook et al include the stabilization of vitamins, essential oils, ketones and ethers.

Normant in U.S. Pat. No. 3,560,531 issued Feb. 2, 1971, describes metallation of materials having active hydrogens including phenothiazine. U.S. Pat. No. 3,344,068 issued Sep. 26, 1967, to Waight et al describes antioxidants for ester-based lubricants. Waight et al's compounds have an N-hydrocarbyl substituted phenothiazine structure. The N-substituted phenothiazine compounds of Waight et al are also substituted in at least one position on the fused aromatic nuclei. A second required component in the compositions of Waight et al is a secondary aromatic amine having two aromatic groups attached to the nitrogen atom.

The preparation of alkylthioalkanols which are useful as intermediates for preparing the compounds of the present invention are described in U.S. Pat. No. 4,031,023 to Musser et al. The Musser et al patent was issued Jun. 21, 1977 and is assigned to The Lubrizol Corporation.

U.S. Pat. No. 2,914,527 to Winthrop et al which issued Nov. 24, 1959, describes pharmaceutical compounds such as omega-(10-phenothiazinyl)alkyl di-alkyl sulfonium salts which are useful as spasmolytics and in particular antihistaminics. U.S. Pat. No. 3,376,224 issued Apr. 2, 1968 to Elliott et al describes phenothiazine derivatives which are stated to be N-substituted methylene compounds which contain an ether linkage between the methylene group and an alkyl or cycloalkyl radical. According to Elliot et al, the alkyl or cycloalkyl radical may carry an alkoxy or other non-reactive substituent.

It has been found in the present invention that the antioxidant activity of a phenothiazine is significantly improved by the presence of a sulfur-containing hydrocarbyl moiety as a substituent on the phenothiazine nitrogen atom. The effectiveness is particularly enhanced when the sulfur atom of the substituent group is in a beta position (i.e., 2-atoms removed) from the phenothiazine N-atom. Such compounds as later described herein have excellent anti-oxidant properties in lubricating oils.

Throughout the specification and claims, percentages and ratios are by weight, temperatures are degrees Celsius, and pressures are in Kpascals gauge unless otherwise indicated. References cited herein are incorporated by reference to the extent that they are applicable.

SUMMARY OF THE INVENTION

The present invention describes phenothiazine derivatives comprising compositions of the formula:

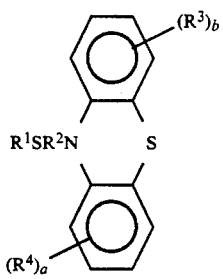

wherein $R^1$ is selected from the group consisting of higher alkyl, or an alkenyl, aryl, alkaryl and aralkyl and mixtures thereof; $R^2$ is alkylene, alkenylene, and aralkylene and mixtures thereof; $R^3$ and $R^4$ are independently alkyl, alkenyl, aryl, alkaryl, aralkyl, halogen, hydroxyl, alkoxy, and alkylthio, arylthio, fused aromatic rings and mixtures thereof; and a and b are independently 0 or greater.

A further embodiment is a product according to formula I and/or III and a major amount of at least one lubricating oil or at least one fuel. The product of formula I may also be formulated at about 1% to 99% by weight with 1% to 99% by weight of a diluent or solvent A process is described for preparing the compositions herein described by (a) reacting a thio alcohol of the formula $$R^1SR^2OH$$

and, (b) a phenothiazine derivative of the formula

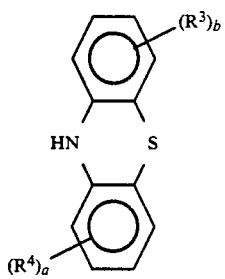

II thereby obtaining the composition of formula I.

Another embodiment of the present invention is the sulfone and sulfoxide derivatives of the aforedescribed compounds wherein $R^1$ is a hydrocarbyl group conveniently selected from the group consisting of an alkyl, alkenyl, aryl, alkaryl and aralkyl and mixtures thereof; $R^2$ is alkylene, alkenylene, and aralkylene and mixtures thereof; $R^3$ and $R^4$ are independently alkyl, alkenyl, aryl, alkaryl, aralkyl, halogen, hydroxyl, alkoxy, aryloxy, alkylthio, arylthio, fused aromatic rings and mixtures thereof; and a and b are independently 0 or greater. Such compounds may be represented by the formula

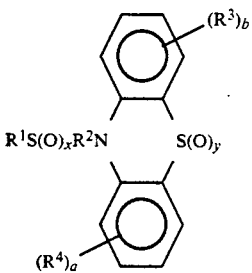

III where a, b, $R^1$, $R^2$, $R^3$ and $R^4$ have the values described above. The values of x and y are independently 0, 1 or 2 and the sum of x and y is greater than or equal to 1.

DETAILED DESCRIPTION OF THE INVENTION

The first aspect of the invention is obtaining the phenothiazine compound or phenothiazine derivative utilized to manufacture the compounds of the present invention. Phenothiazine is itself an article of commerce and, thus, no further description of this material is required.

To obtain the derivatives of phenothiazine useful herein, e.g., where (a) and (b) in formula I are not 0, it is suggested that U.S. Pat. No. 2,781,318 to Cyphers issued Feb. 12, 1957 be consulted. A dialkyl diphenyl amine treated with sulfur at elevated temperatures, such as in the range of 145° C. to 205° C. for a sufficient time to complete the reaction, gives compounds which may be derivatized within the scope of formula I. Conveniently, a catalyst such as iodine may be utilized to establish the sulfur bridge. The reaction is essentially clean and does not affect the amine hydrogen in the composition. Typically, a dialkylated product will be obtained, e.g., where both (a) and (b) are each 1. The monoalkylated phenothiazine derivatives are conveniently obtained by utilizing a monoalkylated diphenylamine which is then cyclized to obtain the corresponding monoalkylated phenothiazine. Similarly, phenothiazine may be alkylated with olefins using a Lewis acid catalyst.

While the derivatives $R^3$ and $R^4$ have been defined above as alkyl, any hydrocarbyl group may be employed. It is convenient to utilize alkenyl, aryl, alkaryl, aralkyl, halogen, hydroxyl, alkoxy, alkylthio, arylthio and the like for $R^3$ and $R^4$ To obtain the hydroxyl derivative one would react, for example, aniline and hydroquinone to form 4-hydroxydiphenylamine which is then cyclized with sulfur. The corresponding alkoxy compounds may be obtained by reacting the hydroxy-containing phenothiazine with an alkyl halide.

Similar to obtaining the alkyl derivatives as $R^3$ and $R^4$, the alkenyl, aryl, alkaryl, aralkyl, and fused ring derivatives may be prepared. The fused ring derivatives may be prepared from phenyl napthylamines which may be cyclized by sulfurization to produce benzophenothiazines. Moreover, the corresponding polyaromatic compounds and their alkyl derivatives are obtained in a similar fashion. The halogenated forms of the product are obtained by treatment of phenothiazine with, for example, bromine or chlorine. The values for $R^3$ and $R^4$ as alkylthio and arylthio are conveniently obtained by treatment of phenothiazine with thiourea and iron chloride. Hydrolysis of the prior obtained isothiuronium chloride to thiophenol which is then alkylated as previously described gives $R^3$ ($R^4$) as alkylthio.

Of course, mixtures of the varying values of $R^3$ and $R^4$ are included within the scope of the present invention. Thus, $R^3$ may be a chloro group, while $R^4$ is an alkyl group The present invention as previously noted also allows for $R^3$ and $R^4$ to independently be different alkyl groups. That is, $R^3$ and $R^4$, while both being alkyl, can be of different carbon chain lengths. The position of $R^3$ and $R^4$ alkyl groups on the aromatic rings will typically be in the para position to the heterocyclic nitrogen, although para substitution to the heterocyclic sulfur may also occur. It is also convenient to utilize derivatives where $R^3$ and $R^4$ are independently aryl. Conveniently, $R^3$ and $R^4$ as hydrocarbyl moieties will contain from about 3 to about 30 carbon atoms in each moiety. Preferably, $R^3$ and $R^4$ as hydrocarbyls will contain independently from about 4 to about 15 carbon atoms.

The second portion of the claimed structure in the present invention provides for the definition of $R^2$. The value, $R^2$ may be an alkylene or alkenylene and conveniently contains in either instance from about 1 to about 18 carbon atoms. Preferably, $R^2$ is a linear alkylene and contains from about 2 to about 8 carbon atoms, most preferably 2 carbon atoms, e.g., ethylene. The value of $R^2$ may also be satisfied by branched chain or substituted material e.g., typically one in which a methyl group is attached to a short chain alkylene group between the sulfur and the nitrogen. That is, the 1-methyl and 2-methyl ethylene derivatives are contemplated herein. $R^2$ may also be aralkylene such as a phenyl residue pendent from an ethylene moiety between the sulfur and the ring nitrogen.

The value of $R^1$ is conveniently defined as a higher alkyl, or an alkenyl, aryl, alkaryl or aralkyl or mixtures thereof. The preferred linkage for $R^1$ to the sulfur is primary. To obtain the compounds of formula I, the reaction of $R^1SCH_2CH_2OH$ with phenothiazine is conveniently utilized. A large number of raw materials may be used to prepare the compounds described herein. For example, in the compounds of formula I, $R^1$ may contain from about 4 to about 50 carbon atoms. Substantial branching may occur in the backbone of the materials utilized to form the $R^1$ residue. The residue $R^1$ is also conveniently obtained containing from about 6 to about 20 carbon atoms in formula I. Where the sulfones and sulfoxides are obtained from the compounds of formula I, the value of $R^1$ is conveniently from about 1 to about 50 carbon atoms, preferably from about 4 to about 50 carbon atoms, most preferably from about 6 to about 20 carbon atoms.

A suggested species for $R^1$ herein is:

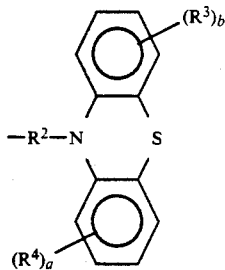

IV which is derived from the reaction of thiodiethanol and phenothiazine.

It is desirable that an oleophilic group be present in the product pendant from the nitrogen atom in the phenothiazine to ensure oil solubility or dispersability. Ordinarily, the oleophilic group is supplied by $R^1$. Alternatively, the values of $R^3$ and $R^4$ may be adjusted to increase the oleophilic nature of the product and to minimize the need for an oleophilic chain corresponding to $R^1$ in the molecule. It is also highly desirable for inhibitor performance that the pendant sulfur be in the beta position to the nitrogen in the phenothiazine structure.

It is to be understood that the values $R^1$, $R^2$, $R^3$ and $R^4$ may contain additional hetero atoms or hetero groups including such moieties as amine, sulfides, phenols, ether linkages, amides, carboxyls and the like. Such groups, as long as they allow functioning of the desired anti-oxidant properties may be included at any level within the various $R^1$-$R^4$ groups, preferably at not greater than 20% by weight of the respective group.

The sulfones and the sulfoxides of the phenothiazine derivatives (formula I) may be obtained by partially or fully oxidizing the sulfur atoms within the molecule. In Formula I, both sulfur atoms are susceptible to oxidation to sulfoxide and sulfones so that both may participate in the anti-oxidant process. Both of the sulfur atoms undergo oxidation to the sulfoxide simultaneously. It then depends on the relative activity of the sulfoxide groups as to whether the ring sulfoxide is then changed to a sulfone or whether the side chain sulfoxide is oxidized to the sulfone. The sulfone formation is dependent upon the sulfoxide formation and, thus, mixtures of the sulfones and the sulfoxides are often obtained. The benefit of the sulfone and sulfoxide derivatives is that they provide additional anti-oxidant properties. The sulfone is a useful compound in that it may undergo further oxidation thus prolonging the protection of the lubricant against degradation.

A convenient mixture of the compound of formula I and the sulfones and sulfoxides is typically obtained in a ratio of from about 1: 0.1: 0.1 to about 0.5: 1:1.

The types of lubricating oils which may be utilized herein are described as being of a lubricating viscosity and may be based on natural oils, synthetic oils, or mixtures thereof. The lubricating oils are also a preferred diluent for use herein.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_3$-$C_8$ fatty acid esters, or the $C_{13}OXO$ acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butyl-phenyl)silicate, hexyl-(4-methyl-2-pentoxy)disiloxane, poly(methyl)siloxans, poly(methylphenyl)siloxanes, etc.). Other synthetic lubricating oils include liquid esters of phosphorus-containing acids (e.g., tricresyl phosphate, trioxtyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the concentrates of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil.

Refined oils are similar to the unrefined oils except they have been further treated in one or more purification steps to improve one or more properties. Many such purification techniques are known to those skilled in the art such as solvent extraction, secondary distillation, hydrotreating, hydrocracking, acid or base extraction, filtration, percolation, etc.

Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products. Most preferably, the oil used herein is a petroleum derived oil.

The fuels which may be treated with the composition of this invention include both solid and normally liquid fuels. That is, the antioxidant effect of the fuels prevents the fuel from degrading prior to the combustion process. By eliminating or minimizing oxidation of the fuel, the fuel value (caloric content) of the fuel remains higher. It may also be observed under certain situations that the fuel by being more stable is less prone to spontaneous combustion. Among the solid fuels which may be utilized are coal, shale, peat, wood, organic refuse, charcoal and the like. Liquid fuels encompass the lighter petroleum fractions such as gasoline, kerosene, and the like as well as other fractions such as middle distillate fuel oils. Typical middle distillate fuel oils which may be treated with the compositions of this invention include Number 1,2 and 4 oils as defined by ANSI/ASTM Standard D-396-79 and other such materials. Combinations of such fuel oils with straight run, vacuum run, and other specially treated residual oils can also be advantageously treated with the compositions of the present invention.

The lubricants and fuels of the present invention may include all matter of typically included ingredients such as dyes, adjuvants, dispersants, other antioxidants, overbased materials and the like. Fuels may also include cetane improvers and octane enhancers. Greases may also benefit from the anti-oxidants described herein.

A further description of the process by which the compounds herein may be formed is as follows.

The phenothiazine and its various derivatives are converted to the compounds of formula I by contacting the phenothiazine compound of formula II with the desired thio alcohol of the formula $R^1SCH_2CH_2OH$. The thio alcohol may be obtained by the reaction of the mercaptan, $R^1SH$ with ethylene oxide under basic conditions. Alternatively, the thio alcohol is obtained by reacting the corresponding terminal olefin with mercaptoethanol under free radical conditions such as by using, for example, 2,2'-azobis (isobutyronitrile) as an initiator.

The reaction conditions for obtaining the formula I compounds include the use of an inert solvent such as toluene, benzene, and the like. A strong acid catalyst such as sulfuric acid or para-toluene sulfonic acid at about 1 part to 50 parts per 1000 parts of the phenothiazine is suggested. The reaction is conducted under an inert gas blanket. The temperature conditions are conveniently set at the reflux temperature with removal of the water as it is formed. Conveniently, the reaction temperature is maintained between 80° C. and 170° C.

The amount of the diluent or solvent utilized herein to prepare a concentrate is typically that amount needed to solubilize or disperse the compound of Formula I. Typically, the diluent or solvent is present at about 1% to 99% by weight, conveniently at about 60% to 99% by weight of the composition. The phenothiazine derivatives described herein are useful at about 0.1% to 10% by weight in a fully formulated product. Suggested diluents and solvents are those lubricants and fuels in which the compounds of formula I will eventually be added. Any other diluent or solvent may be used provided that such does not interfere substantially with the function of the end product. Oxidation of the compounds of formula I to the sulfone and sulfoxide occurs naturally under crankcase conditions. If the sulfone and sulfoxide are desired as discrete compounds, they may be obtained by using an oxidant such as hydrogen peroxide. The compounds of formula I are converted to the sulfone or sulfoxide in a solvent such as glacial acetic acid or ethanol under an inert gas blanket. The partial oxidation takes place conveniently at about 20° to 150° C. The degree of sulfone and sulfoxide formation is determined by practice.

Oxidation of lubricants occur due to heat and shear action on the lubricating oil in the presence of oxygen and other oxidants. In the absence of antioxidants, the lubricating oil will build up viscosity, deposits will form on engine parts, and corrosive acids form, all of which are detrimental to engine performance and life. The use of antioxidants such as the type described herein are particularly helpful in reducing carbon radicals, carbon peroxy radicals, and or peroxides which are formed in the lubricating product.

The following are examples of the present invention.

EXAMPLE I

One mole of phenothiazine is placed in a one liter, round bottom flask with 300 ml of toluene. The reactants are maintained under a nitrogen blanket. To the mixture of phenothiazine and toluene is added 0.05 mole of sulfuric acid catalyst. The mixture is then heated to reflux temperature and 1.1 moles of n-dodecylthioethanol is added dropwise over a period of approximately 90 minutes. Water is continuously removed as it is formed in the reaction process.

The reaction mixture is continuously stirred under reflux until substantially no further water is evolved. The reaction mixture is then allowed to cool to 90° C. The sulfuric acid catalyst is neutralized with sodium hydroxide. The solvent is then removed under a vacuum of 2 KPa at 110° C. The residue is filtered giving a 95% yield of the desired product. The product has a purity of greater than 90% of the desired compound.

The compound is identified as having the value of $R^1$ as $C_{12}$, $R^2$ being ethylene, and both a and b are zero (e.g., the aromatic rings of the phenothiazine contain only hydrogen substitution).

EXAMPLE II

One mole of phenothiazine is placed in a one liter, round bottom flask with 300 ml of toluene. The reactants are maintained under a nitrogen blanket. To the mixture of the phenothiazine and toluene is added 0.05 mole of sulfuric acid as a catalyst. The mixture is then heated to reflux temperature and 1.1 moles of n-hexylthioethanol is added dropwise over a period of approximately 90 minutes. Water is continuously removed as it is formed in the reaction process.

The reaction mixture is continuously stirred under reflux until substantially no more water is evolved. The reaction mixture is then allowed to cool to 90° C. The sulfuric acid catalyst is neutralized with sodium hydroxide. The solvent is then removed under a vacuum of 2 KPa at 110° C. The residue is filtered giving a 95% yield of the desired product. The product has a purity of greater than 90% of the desired compound.

The compound is identified as having the value of $R^1$ as $C_6$, $R^2$ being ethylene, and both a and b are zero. A similar result will be obtained when using n-octylthioethanol.

EXAMPLE III

Phenothiazine is alkylated with nonene, using aluminum chloride as a Friedel Crafts catalyst under conventional conditions. One mole of the dialkylated phenothiazine is placed in a one liter round bottom flask with 300 milliters of toluene. A nitrogen sparge and blanket are employed. To the mixture of the dialkylated phenothiazine and toluene is added 0.05 mole of sulfuric acid as a catalyst. The mixture is then heated to reflux and 1.1 moles of n-dodecylthioethanol is added dropwise over a period of approximately 90 minutes. Water is continuously removed as it is formed.

The reaction mixture is continually stirred under reflux until substantially no further water is obtained. The reaction mixture is then allowed to cool to 90° C. The sulfuric acid catalyst is neutralized with sodium hydroxide. The solvent is then removed under a vacuum of 2 KPa at 110° C. The residue is then filtered giving a 95% yield of the desired product. The product has a purity of greater than 80% of the desired compound.

The compound is identified as having the value of $R^1$ being $C_{12}$, and $R^3$ and $R^4$ being in the para position as $C_9$, $R^2$ is ethylene and a and b are each one.

A modification of this example is to use dodecyl mercaptan which is pre-reacted with styrene oxide under basic conditions. The substitution of this reactant above gives $R^2$ as a ethylene group substituted with a pendent phenyl group.

EXAMPLE IV

One mole of phenyl alpha-naphthylamine is placed in a one liter round bottom flask. A nitrogen sparge is applied to flush air from the reaction vessel. The reactants are maintained under the nitrogen blanket. The amine is first sulfurized at 190° C. with an iodine catalyst under conventional conditions. Then, 1.1 moles of n-stearyl thioethanol is utilized to alkylate the sulfurized product in 300 ml toluene using a small amount of sulfuric acid catalyst. The reaction is allowed to proceed over a period of 90 minutes. Water is continuously removed as it is formed in the reaction process. The reaction mixture is continually stirred at reflux until substantially no more water is evolved. The reaction mixture is then allowed to cool to 90° C. The sulfuric acid catalyst is then neutralized with sodium hydroxide. The solvent is then removed under a vacuum of 2 KPa at 110° C. to give the benzophenothiazine product.

EXAMPLE V

One mole of phenothiazine is placed in a one liter, round bottom flask with 300 ml of toluene. The reaction is maintained under a nitrogen blanket. To the mixture of the phenothiazine and toluene is added 0.05 mole of sulfuric acid as a catalyst. The mixture is then heated to reflux temperature and 1.1 moles of phenylthioethanol is added dropwise over a period of approximately 90 minutes. The phenylthiothethanol is obtained from the reaction of thiophenol and ethylene oxide with a basic catalyst. Water is continuously removed as it is formed in the reaction process.

The reaction mixture is continuously stirred under reflux until substantially no further water is evolved. The reaction mixture is then allowed to cool to 90° C. The sulfuric acid catalyst is neutralized with sodium hydroxide. The solvent is then removed under a vacuum of 2 KPa at 110° C. The residue is filtered giving a 95% yield of the desired product. The product has a purity of greater than 90% of the desired compounds.

The compound of this example is identified as having $R^1$ as phenyl, $R^2$ being ethylene, and both a and b are zero. (e.g., the aromatic rings contain only hydrogen substitutions).

EXAMPLE VI

Two moles of the dialkylated phenothiazine of Example III are placed in a two liter, round bottom flask with 600 ml of toluene. The reaction is maintained under a nitrogen blanket. To the mixture of the alkylated phenothiazine derivative and toluene is added 0.1 mole of sulfuric acid as a catalyst. The mixture is then heated to reflux temperature and 1.1 moles of thiodiethanol is added dropwise over a period of approximately 90 minutes. Water is continuously removed as it is formed in the reaction process.

The reaction mixture is continuously stirred under reflux until substantially no more water is evolved. The reaction mixture is then allowed to cool to 90° C. The sulfuric acid catalyst is neutralized with sodium hydroxide. The solvent is then removed under a vacuum of 2 KPa at 110° C. The residue is filtered giving a 95% yield of the desired product. The product has a purity of greater than 80% of the desired compound.

The compound obtained is identified as having a symmetrical bis-phenothiazine structure, $R^2$ is ethylene, a and b are each 1 with $R^3$ and $R^4$ being nonyl. This product is generally described as:

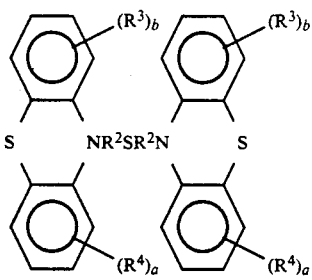

EXAMPLE VII

The oxidized product of Example I is obtained by placing 0.2 mole of the product therein in a one liter round bottom flask. Ethanol in the amount of 400 ml is then added, followed by a nitrogen sparge. An inert gas blanket is thereafter retained during the reaction. The reaction is then heated to reflux and 30% hydrogen peroxide (0.2 mole) is added dropwise over one-half hour. The reaction is stirred under reflux for 5 hours.

The product is then allowed to cool and water in the amount of 400 ml is mixed with the product. The lower organic layer is separated, dried with magnesium sulfate, and the residual solvent removed at 100° C. at 2 Kpa. The corresponding oxidized product of Example I is thus obtained.

EXAMPLE VIII

A series of lubricant products are prepared by mixing an SAE 30 motor oil in the amount of 1000 parts with 50 parts each of the products of Example I–VII. The resultant products show desirable antioxidant activity and lubricant activity. Mixtures of products I and VII in equal amounts are desirable in this example.

EXAMPLE IX

Number 2 diesel fuel in the amount of 1000 parts is treated with 50 parts of each of the products of Examples I–VII to give a fuel which is resistant to storage temperature oxidation.

EXAMPLE X

A series of blends are made for lubricant top treatments of phenothiazine derivatives. The base oil used is 10W30 motor oil. The blends are tested for oxidation stability using Pressure Differential Scanning Calorimetry. Time is measured in minutes to the exotherm peak maximum. All phenothiazine products have a $R_2=C_2H_4$, $a=0$, $b=0$, and are employed at equal sulfur level.

| TEST | $R_1 =$ | TREATMENT LEVEL % | TIME |
|---|---|---|---|
| 1 | n-C$_6$H$_{13}$ | 0.40 | 42 |
| 2 | n-C$_8$H$_{17}$ | 0.43 | 48 |
| 3 | n-C$_{12}$H$_{25}$ | 0.50 | 35 |
| 4* | n-C$_{12}$H$_{25}$ | 0.50 | 48 |
| 5* | n-C$_{12}$H$_{25}$ | 0.50 | 51 |
| 6 | No Additive | -0- | less than 15 |
| 7 | IIID Engine Test borderline fail for a fully formulated package | | 26 |

*Products 4 and 5 are prepared according to Example VII by using H$_2$O$_2$ at 1 mole and 2 moles per mole of the phenothiazine derivative, respectively.

The test results show the products of the invention exceed the minimum requirements for a IIID engine test pass.

EXAMPLE XI

A series of blends are made using Union West 90N oil. In these fully formulated blends, the phenothiazine compounds replaced the sulfur and nitrogen oxidation inhibitors normally present in an automatic transmission fluid.

These blends are tested for air oxidation measuring hours to failure.

All the phenothiazine compounds in the table have $R_2=C_2H_4$, $a=0$, $b=0$, and are employed at equal sulfur level.

| TEST | $R_1 =$ | TREATMENT LEVEL % | HOURS TO FAILURE |
|---|---|---|---|
| 1 | n-hexyl | 0.38 | 105 |
| 2 | n-octyl | 0.41 | 105 |
| 3 | n-dodecyl | 0.52 | 105 |

The fully formulated products of the invention are equivalent in perfomance to a conventional automatic transmission fluid which uses a 0.6% conventional oxidation inhibitor package.

What is claimed is:

1. A process for preparing a composition of the formula

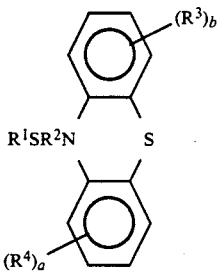

including the step of reacting
(a) a thio alcohol of the formula $R^1SR^2OH$ and
(b) a phenothiazine of the formula

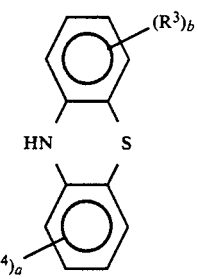

II wherein $R^1$ is selected from the group consisting of alkyl, alkenyl, aryl, alkaryl, and aralkyl groups; $R^2$ is selected from the group consisting of alkylene, alkenylene, and aralkylene groups; $R^3$ and $R^4$ are independently selected from the group consisting of alkyl, alkenyl, aryl, alkaryl, aralkyl, halogen, hydroxyl, alkoxy, aryloxy, alkylthio, arylthio, and fused aromatic ring groups, substituents $R^1$ through $R^4$ optionally containing additional hetero atoms or hetero groups, and wherein a and b are independently 0 or greater.

* * * * *